(12) United States Patent
Buderer et al.

(10) Patent No.: US 9,301,936 B2
(45) Date of Patent: Apr. 5, 2016

(54) PHARMACEUTICAL FORMULATIONS OF TRANEXAMIC ACID AND THEIR USE

(71) Applicant: Imprimis Pharmaceuticals, Inc., San Diego, CA (US)

(72) Inventors: Matthew James Buderer, Oak Harbor, OH (US); Jeffrey Joel Abrams, San Diego, CA (US)

(73) Assignee: Imprimis Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 14/325,630

(22) Filed: Jul. 8, 2014

(65) Prior Publication Data

US 2015/0038406 A1 Feb. 5, 2015

Related U.S. Application Data

(60) Provisional application No. 61/951,916, filed on Mar. 12, 2014, provisional application No. 61/917,071, filed on Dec. 17, 2013, provisional application No. 61/843,705, filed on Jul. 8, 2013.

(51) Int. Cl.
| | |
|---|---|
| *A61K 38/00* | (2006.01) |
| *A01N 37/18* | (2006.01) |
| *A61K 31/195* | (2006.01) |
| *A61K 31/167* | (2006.01) |
| *A61K 31/19* | (2006.01) |
| *A61K 31/245* | (2006.01) |
| *A61K 31/407* | (2006.01) |
| *A61K 31/7048* | (2006.01) |
| *A61K 38/12* | (2006.01) |
| *A61K 45/06* | (2006.01) |
| *A61K 9/06* | (2006.01) |
| *A61K 9/00* | (2006.01) |
| *A61K 9/02* | (2006.01) |
| *A61K 31/18* | (2006.01) |
| *A61K 31/351* | (2006.01) |
| *A61K 31/65* | (2006.01) |

(52) U.S. Cl.
CPC ............ *A61K 31/195* (2013.01); *A61K 9/0019* (2013.01); *A61K 9/0031* (2013.01); *A61K 9/0034* (2013.01); *A61K 9/0043* (2013.01); *A61K 9/02* (2013.01); *A61K 9/06* (2013.01); *A61K 31/167* (2013.01); *A61K 31/18* (2013.01); *A61K 31/19* (2013.01); *A61K 31/245* (2013.01); *A61K 31/351* (2013.01); *A61K 31/407* (2013.01); *A61K 31/65* (2013.01); *A61K 31/7048* (2013.01); *A61K 38/12* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2003/0175328 A1 | 9/2003 | Shefer et al. | |
| 2005/0267014 A1* | 12/2005 | Rojkjaer | 514/2 |
| 2007/0026052 A1* | 2/2007 | Baggett | 424/443 |
| 2007/0258971 A1 | 11/2007 | Heslet et al. | |
| 2008/0171074 A1 | 7/2008 | Oltarzhevskaya et al. | |
| 2012/0045518 A1 | 2/2012 | Nielsen et al. | |
| 2012/0302640 A1 | 11/2012 | MacAlister | |

FOREIGN PATENT DOCUMENTS

WO WO 2013/040080 * 3/2013

OTHER PUBLICATIONS

Chatterjee, Water-soluble carbon monoxide-releasing molecules: helping to elucidate the vascular activity of the 'silent killer', British Journal of Pharmacology (2004) 142, 391-393.*

Houri-Haddad et al, Inflammatory response to chlorhexidine, minocycline HCl and doxycycline HCl in an in vivo mouse model, J Clin Periodontol. Sep. 2008;35(9):783-8.*

International Search Report with Written Opinion corresponding to International Patent Application No. PCT/US2014/045706, mailed Oct. 22, 2014.

* cited by examiner

*Primary Examiner* — Karlheinz R Skowronek
*Assistant Examiner* — Sergio Coffa
(74) *Attorney, Agent, or Firm* — Lathrop & Gage LLP

(57) ABSTRACT

The present invention relates to pharmaceutical formulations comprising tranexamic acid, kits thereof, and methods for treating bleeding by local administration.

39 Claims, No Drawings

PHARMACEUTICAL FORMULATIONS OF TRANEXAMIC ACID AND THEIR USE

CROSS-REFERENCE TO RELATED APPLICATIONS

This application claims priority under 35 U.S.C. §119(e) to each of the following U.S. Provisional Applications No. 61/843,705 filed on Jul. 8, 2013 entitled "Pharmaceutical Formulations of Tranexamic Acid, and Their Use"; No. 61/917,071 filed on Dec. 17, 2013 entitled "Pharmaceutical Formulations of Tranexamic Acid and Their Use"; and No. 61/951,916 filed on Mar. 12, 2014 entitled "Pharmaceutical Formulations of Tranexamic Acid and Their Use" the entire contents of each of which are hereby incorporated by reference.

FIELD OF USE

The present disclosure relates to pharmaceutical formulations comprising tranexamic acid, and methods for treating bleeding by local administration.

BACKGROUND OF THE INVENTION

The global demographic is changing with people living longer and being subject to anti-coagulant therapy. In certain embodiments, patients receiving anti-coagulant therapy can also be immune compromised. Compositions are necessary for increasing coagulation locally for treatment of cuts, scrapes, abrasions and burns in those who are receiving anti-coagulant therapy while also providing an anti-bacterial effect.

SUMMARY OF THE INVENTION

Provided herein are compositions consisting essentially of a therapeutically effective amount of tranexamic acid, one or more antibiotics, and an excipient or carrier that facilitates local administration, and methods of use thereof for treating bleeding in a subject in need thereof comprising locally administering to the subject the compositions.

Provided herein are also kits comprising a pharmaceutical composition consisting essentially of a therapeutically effective amount of tranexamic acid, and one or more antibiotics; an excipient or carrier that facilitates local administration; two or more containers for housing the composition and the excipient or carrier; and instructions for use.

In another aspect, provided herein are pharmaceutical compositions comprising a therapeutically effective amount of tranexamic acid and an excipient or carrier that facilitates transdermal administration, and methods of use thereof for treating bleeding in a subject in need thereof comprising transdermally administering to the subject the compositions. The pharmaceutical compositions can further comprise one or more antibiotics. In one particular embodiment, the pharmaceutical composition consists essentially of a therapeutically effective amount of tranexamic acid, one or more antibiotics, and an excipient or carrier that facilitates transdermal administration.

In still another aspect, provided herein are kits comprising a pharmaceutical composition comprising a therapeutically effective amount of tranexamic acid; an excipient or carrier that facilitates transdermal administration; two or more containers for housing the composition and the excipient or carrier; and instructions for use. The pharmaceutical compositions can further comprise one or more antibiotics. In one particular embodiment, the pharmaceutical composition consists essentially of a therapeutically effective amount of tranexamic acid, one or more antibiotics, and an excipient or carrier that facilitates transdermal administration.

The tranexamic acid can be between 1 and 70% by weight of the pharmaceutical composition.

In yet another aspect, the pharmaceutical compositions may further optionally include therapeutically effective quantity(ies) of one or several anesthetic(s) and/or one or several non-steroid anti-inflammatory drug(s) (NSAID's).

The antibiotics can be, e.g., sulfacetamide, mupirocin, erythromycin, sulfadiazine, mafenide, tetracycline, bacitracin, neomycin, or polymyxin B. In certain particular embodiments, the one or more antibiotics are a triple antibiotic. The triple antibiotic can be, e.g., bacitracin, neomycin, and polymyxin B. The anesthetics can be, e.g., lidocaine, proparacaine, procaine or tetracaine and NSAID's can be e.g., ketorolac, ketoprofen, flurbiprofen, bromfenac or diclofenac.

The excipient or carrier can help facilitate the composition to remain in contact with a bleeding wound. Non-limiting examples of the excipient or carrier are ointments, creams, liniments, pastes, patches, lotions, gels, shampoos, hydrogels, liposomes, sprays, aerosols, solutions, sponges, films, plasters, surgical dressings, bandages, or emulsions.

In other embodiments, the excipient or carrier permits instillation of the composition, such as nasal instillation, rectal instillation, and bladder instillation.

The composition can be a transdermal composition, such as an ointment, a gel, a liniment, a paste, a film, a hydrogel, a liposome, a cream, a patch, and a spray.

In certain embodiments of the methods provided herein, the composition are administered to a subject to whom an anticoagulant, such as heparin and warfarin, has been or is to be administered.

In certain embodiments of the kits provided herein, the excipient or carrier is an apparatus for topical administration, such as a patch, a sponge, a film, a surgical dressing, a spray, and a bandage.

The disclosure further provides a pharmaceutical composition consisting essentially of a therapeutically effective amount of tranexamic acid; one or more antibiotic(s); optionally, one or more anesthetic(s); optionally, one or more non-steroid anti-inflammatory drug(s); and an excipient or carrier that facilitates local administration. In one embodiment, the therapeutically effective amount of tranexamic acid is between 1-70% by weight of the composition.

In another embodiment, the one or more antibiotic(s) are selected from sulfacetamide, mupirocin, erythromycin, sulfadiazine, mafenide, tetracycline, bacitracin, neomycin, and polymyxin B. Optionally, the one or more antibiotic(s) are selected from bacitracin, neomycin, and polymyxin B.

In another embodiment, the excipient or carrier permits the composition to remain in contact with a bleeding wound. In certain aspects of this embodiment, the excipient or carrier comprises an ointment, a cream, a liniment, a paste, a patch, a lotion, a gel, a shampoo, a hydrogel, a liposome, a spray, an aerosol, a solution, a sponge, a film, a plaster, a surgical dressing, a bandage, or an emulsion.

In another embodiment, the excipient or carrier permits instillation of the composition, wherein the instillation is selected from nasal instillation, rectal instillation, and bladder instillation.

In another embodiment, the one or more anesthetic(s) are selected from lidocaine, proparacaine, procaine, tetracaine and combinations thereof. In another embodiment, the one or more non-steroid anti-inflammatory drug(s) are selected from ketorolac, ketoprofen, flurbiprofen, bromfenac, diclofenac and combinations thereof.

In another embodiment, the composition is a transdermal composition. In one aspect of this embodiment, the transdermal composition is selected from an ointment, a gel, a liniment, a paste, a film, a hydrogel, a liposome, a cream, a patch, and a spray.

In another embodiment, the transdermal composition is a non-musosal composition. In another embodiment, the transdermal composition is a non-oral composition.

The disclosure also provides a method for treating bleeding in a subject in need thereof comprising locally administering to the subject the pharmaceutical composition described above. In one embodiment of this method, the therapeutically effective amount of tranexamic acid is between 1-70% by weight of the composition.

In another embodiment of this method, the one or more antibiotics are selected from sulfacetamide, mupirocin, erythromycin, sulfadiazine, mafenide, tetracycline, bacitracin, neomycin, and polymyxin B. Optionally, the one or more antibiotics are bacitracin, neomycin, and/or polymyxin B.

In another embodiment of this method, an anticoagulant has been or is to be administered to the subject.

In another embodiment of this method, the excipient or carrier permits the composition to remain in contact with said bleeding wound. In one aspect of this embodiment, the excipient or carrier comprises an ointment, a cream, a liniment, a paste, a patch, a lotion, a gel, a shampoo, a hydrogel, a liposome, a spray, an aerosol, a solution, a sponge, a film, a plaster, a surgical dressing, a bandage, or an emulsion.

In another embodiment of this method, the excipient or carrier permits administering the composition by an instillation, wherein the instillation is selected from nasal instillation, rectal instillation, and bladder instillation.

In another embodiment of this method the one or more anesthetic(s) are selected from lidocaine, proparacaine, procaine, tetracaine and combinations thereof. In another embodiment of this method, the one or more non-steroid anti-inflammatory drug(s) are selected from ketorolac, ketoprofen, flurbiprofen, bromfenac, diclofenac and combinations thereof.

In another embodiment of this method, the pharmaceutical composition is a transdermal composition. In one aspect of this embodiment, the transdermal composition is selected from an ointment, a gel, a liniment, a paste, a film, a hydrogel, a liposome, a cream, a patch and a spray.

In another embodiment of this method, the composition is administered non-musosally. In another embodiment of this method, the composition is administered non-orally.

The disclosure also provides a kit comprising the pharmaceutical composition described above; two or more containers for housing the composition; and instructions for use. In one embodiment of this kit, the therapeutically effective amount of tranexamic acid is between 1-70% by weight of the composition.

In another embodiment of this kit, the one or more antibiotics are selected from sulfacetamide, mupirocin, erythromycin, sulfadiazine, mafenide, tetracycline, bacitracin, neomycin, and polymyxin B. Optionally, the one or more antibiotics are bacitracin, neomycin, and/or polymyxin B.

In another embodiment of this kit, an anticoagulant has been or is to be administered to the subject.

In another embodiment of this kit, the excipient or carrier permits the composition to remain in contact with said bleeding wound. In one aspect of this embodiment, the excipient or carrier comprises an ointment, a cream, a liniment, a paste, a patch, a lotion, a gel, a shampoo, a hydrogel, a liposome, a spray, an aerosol, a solution, a sponge, a film, a plaster, a surgical dressing, a bandage, or an emulsion.

In another embodiment of this kit, the excipient or carrier permits administering the composition by an instillation, wherein the instillation is selected from nasal instillation, rectal instillation, and bladder instillation.

In another embodiment of this kit the one or more anesthetic(s) are selected from lidocaine, proparacaine, procaine, tetracaine and combinations thereof. In another embodiment of this kit, the one or more non-steroid anti-inflammatory drug(s) are selected from ketorolac, ketoprofen, flurbiprofen, bromfenac, diclofenac and combinations thereof.

In another embodiment of this kit, the pharmaceutical composition is a transdermal composition. In one aspect of this embodiment, the transdermal composition is selected from an ointment, a gel, a liniment, a paste, a film, a hydrogel, a liposome, a cream, a patch and a spray.

In another embodiment of this kit, the composition is administered non-musosally. In another embodiment of this kit, the composition is administered non-orally.

The disclosure also provides a pharmaceutical composition comprising a therapeutically effective amount of tranexamic acid and an excipient or carrier that facilitates transdermal administration. In one embodiment, the composition further comprises one or more antibiotics.

In another embodiment, the composition consists essentially of a therapeutically effective amount of tranexamic acid, one or more antibiotics, and an excipient or carrier that facilitates transdermal administration. In another embodiment, the therapeutically effective amount of tranexamic acid is between 1-70% by weight of the composition.

In another embodiment, the one or more antibiotics are selected from sulfacetamide, mupirocin, erythromycin, sulfadiazine, mafenide, tetracycline, bacitracin, neomycin, and polymyxin B. In one aspect of this embodiment, the one or more antibiotics are selected from bacitracin, neomycin, and polymyxin B.

In another embodiment, the excipient or carrier permits the composition to remain in contact with a bleeding wound. In one aspect of this embodiment, the excipient or carrier comprises an ointment, a cream, a liniment, a paste, a patch, a lotion, a gel, a shampoo, a hydrogel, a liposome, a spray, an aerosol, a solution, a sponge, a film, a plaster, a surgical dressing, a bandage, or an emulsion.

In another embodiment, the composition is an ointment, a gel, a liniment, a paste, a film, a hydrogel, a liposome, a cream, a patch, or a spray.

The disclosure also provides a method for treating bleeding in a subject in need thereof comprising transdermally administering to the subject a pharmaceutical composition, wherein the composition comprises a therapeutically effective amount of tranexamic acid and an excipient or carrier that facilitates the transdermal administration. In one embodiment, the pharmaceutical composition further comprises one or more antibiotics.

In another embodiment, the pharmaceutical composition consists essentially of a therapeutically effective amount of tranexamic acid, one or more antibiotics, and an excipient or carrier that facilitates transdermal administration.

In another embodiment, the therapeutically effective amount of tranexamic acid is between 1-70% by weight of the composition.

In another embodiment, the one or more antibiotics are selected from sulfacetamide, mupirocin, erythromycin, sulfadiazine, mafenide, tetracycline, bacitracin, neomycin, and polymyxin B. In one aspect of this embodiment, the one or more antibiotics are bacitracin, neomycin, and/or polymyxin B.

In another embodiment, an anticoagulant has been or is to be administered to the subject.

In another embodiment, the excipient or carrier permits the composition to remain in contact with said bleeding wound. In one aspect of this embodiment, the excipient or carrier comprises an ointment, a cream, a liniment, a paste, a patch, a lotion, a gel, a shampoo, a hydrogel, a liposome, a spray, an aerosol, a solution, a sponge, a film, a plaster, a surgical dressing, a bandage, or an emulsion.

In another embodiment, the composition is an ointment, a gel, a liniment, a paste, a film, a hydrogel, a liposome, a cream, a patch, or a spray.

The disclosure also provides a kit comprising a pharmaceutical composition comprising a therapeutically effective amount of tranexamic acid; an excipient or carrier that facilitates transdermal administration; two or more containers for housing the composition and the excipient or carrier; and instructions for use. In one embodiment, the pharmaceutical composition further comprises one or more antibiotics.

In another embodiment, the pharmaceutical composition consists essentially of a therapeutically effective amount of tranexamic acid, one or more antibiotics, and an excipient or carrier that facilitates transdermal administration.

In another embodiment, the therapeutically effective amount of tranexamic acid is between 1-70% by weight of the composition.

In another embodiment, the one or more antibiotics are selected from sulfacetamide, mupirocin, erythromycin, sulfadiazine, mafenide, tetracycline, bacitracin, neomycin, and polymyxin B. In one aspect of this embodiment, the one or more antibiotics are bacitracin, neomycin, and/or polymyxin B.

In another embodiment, the excipient or carrier permits the composition to remain in contact with a bleeding wound. In one aspect of this embodiment, the excipient or carrier comprises an ointment, a cream, a liniment, a paste, a patch, a lotion, a gel, a shampoo, a hydrogel, a liposome, a spray, an aerosol, a solution, a sponge, a film, a plaster, a surgical dressing, a bandage, or an emulsion.

In another embodiment, the composition is an ointment, a gel, a liniment, a paste, a film, a hydrogel, a liposome, a cream, a patch, or a spray.

In another embodiment, the excipient or carrier is an apparatus for topical administration selected from a patch, a sponge, a film, a surgical dressing, a spray, and a bandage.

DETAILED DESCRIPTION

This disclosure relates to the finding that local administration, e.g., transdermal administration, of an antifibrinolytic, such as tranexamic acid for treatment of bleeding, such as a bleeding resulting from cuts and/or abrasions in a subject's skin. In certain embodiments, the antifibrinolytic is administered with one or more antibiotics that are appropriate for local administration, e.g., transdermal administration. In other embodiments, the antifibrinolytic is administered by bladder instillation, rectal instillation, or nasal instillation.

Accordingly, provided herein include pharmaceutical compositions comprising an antifibrinolytic, such as tranexamic acid, with one or more antibiotics that are appropriate for local administration, such as transdermal administration and instillations (bladder, rectal and nasal), kits thereof, and methods for treating bleeding including, but not limited to, bleeding resulting from cuts and/or abrasions in a subject's skin by local administration.

Definitions

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "an antibiotic" includes a mixture of two or more antibiotics, and reference to "a carrier" includes mixtures of two or more carriers, and the like.

In describing and claiming the present invention, the following terminology will be used in accordance with the definitions set out below.

The term "bleeding" as used herein refers to conditions where blood flows through a break in the skin or mucosa of a subject. Non-limiting examples of bleeding include cuts and abrasions from trauma including from surgery.

The term "minor cuts and abrasions" is intended to include any and all cuts and abrasions that do not require hospitalization. In other embodiments, cuts and abrasions that do not require hospitalization include those that do not require stitches, liquid stitches or butterfly stitches to close and heal.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" bleeding, as the term is used herein, thus encompasses reducing the flow of blood through a break in the skin or mucosa.

By an "effective" amount of a drug or pharmacologically active agent is meant a nontoxic but sufficient amount of the drug or agent to provide the desired effect, e.g., reduction of bleeding.

The terms "local administration" and "locally administering" as used herein refer to treatment of bleeding by administering at sites proximate to the bleeding. In certain embodiments, "local administration" or "locally administering" refers to external administration at the site of a wound. In other embodiments, "local administration" or "locally administering" refers to instillations, such as nasal instillation, bladder instillation, and rectal instillation. Local administration is distinguished from systemic administrations, such as oral administration or intravenous injection, wherein dosage of a pharmaceutical composition is relatively similar throughout the body of a subject.

The term "transdermal" delivery includes both transdermal (or "percutaneous") and transmucosal administration, i.e., delivery by passage of a drug through the body surface, i.e., the skin or mucosal tissue. Examples of conventional transdermal drug delivery systems include transdermal "patches" wherein the agent is typically contained within a laminated structure that serves as a drug delivery device to be affixed to the skin. In such a structure, the drug composition is typically contained in a layer, or "reservoir," underlying an upper backing layer. The laminated device may contain a single reservoir, or it can contain multiple reservoirs. The reservoir can comprise a polymeric matrix of a pharmaceutically acceptable contact adhesive material that serves to affix the system to the skin during drug delivery. Non-limiting examples of suitable skin contact adhesive materials include polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or hydrogel reservoir, or can take some other form.

The term a "non-oral topical composition" means that the composition is not to be used inside the patient's mouth. The term a "non-mucosal composition" means that the composition is not to be used on the mucosal tissue.

The term "topical administration" is used in its conventional sense to mean delivery of a topical drug or pharmacologically active agent to the skin or mucosa. Examples of formulations for topical drug delivery include ointments and creams. Ointments are semisolid preparations which are typically based on petrolatum or other petroleum derivatives. Creams containing the selected active agent include viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and non-sensitizing.

The term "excipient or carrier that facilitates topical administration" refers to excipients or carriers (e.g., pharmaceutically inactive substances) that facilitate the transport of a composition across skin or mucosa or enhances the stability of the location of an administered composition to a particular site on the skin or mucosa. An excipient or carrier facilitates the transport of a composition across skin or mucosa when it increases the rate of transport of a composition above that which the composition would have if administered with water alone. An excipient or carrier enhances the stability of the location of an administered composition to a particular site on the skin or mucosa, when the excipient or carrier holds the composition within 10 mm of the position at which it was administered longer than if the composition was administered with water.

The term "anesthetic" refers to a substance that that causes loss of sensation and therefore induces insensitivity or low sensitivity to pain.

The terms "non-steroid anti-inflammatory drugs" or "NSAID" refer to a class of compounds that are free of any steroid moieties yet are capable of providing analgesic, antipyretic and/or anti-inflammatory effects.

Methods of Treatment

In one aspect, provided herein is a method for treating bleeding in a subject in need thereof, which comprises transdermally administering to the subject a pharmaceutical composition comprising an antifibrinolytic. Antifibrinolytics include aminocaproic acid and tranexamic acid. In one embodiment, the antifibrinolytic is co-administered with one or more antibiotics. In another embodiment, the composition further comprises an excipient or carrier that facilitates transdermal administration.

In another aspect, provided here is a method for treating bleeding in a subject in need thereof, which comprises locally administering to the subject a pharmaceutical composition, wherein the composition consists essentially of or consists of a therapeutically effective amount of tranexamic acid, one or more antibiotics, and an excipient or carrier that facilitates local administration.

In one particular embodiment, provided herein is a method for treating bleeding in a subject in need thereof, comprising transdermally administering to the subject a pharmaceutical composition, wherein the composition consists essentially of or consists of a therapeutically effective amount of tranexamic acid, one or more antibiotics, and an excipient or carrier that facilitates transdermal administration.

In certain embodiments, the bleeding is resulted from a cut or abrasion in the skin or mucosa of a subject. In other embodiment, the bleeding occurs in nose, rectum, or bladder in a subject.

In certain embodiments of the methods described above, the one or more antibiotics are antibiotics that are effective when administered locally. Non-limiting examples of the antibiotics described herein include sulfacetamide, mupirocin, erythromycin, sulfadiazine, mafenide, tetracycline, bacitracin, neomycin, and polymyxin B.

In other embodiments, the one or more antibiotics are a triple antibiotic. The triple antibiotic can include bacitracin, neomycin, and polymyxin B.

In certain other embodiments, the pharmaceutical compositions may further optionally include therapeutically effective quantity(ies) of one or several anesthetic(s) and/or of one or several NSAID's. Non-limiting examples of the suitable anesthetics that can be used include lidocaine, proparacaine, procaine, tetracaine and combinations thereof. Non-limiting examples of the suitable NSAID's that can be used include ketorolac, ketoprofen, flurbiprofen, bromfenac, diclofenac and combinations thereof.

In still other embodiments, the excipient or carrier permits the composition to remain in contact with a bleeding wound. In certain particular embodiments, the excipient or carrier comprises an ointment, a cream, a liniment, a paste, a patch, a lotion, a gel, a shampoo, a hydrogel, a liposome, a spray, an aerosol, a solution, a sponge, a film, a plaster, a surgical dressing, a bandage, or an emulsion.

According to certain embodiments, the compositions described herein are administered topically. In other embodiments, they are administered transdermally. In other embodiments, the compositions described herein are administered at the site of a wound or cut of the skin or mucosa from which blood is flowing.

In certain particular embodiments, the excipient or carrier can comprise one or more of cocoa butter, cottonseed oil, sodium pyruvate, tocopheryl acetate, and petroleum jelly.

In certain particular embodiments, the composition comprises an excipient or carrier that permits instillation of the composition, and the composition is administered by local instillation, such as nasal instillation, rectal instillation, and bladder instillation.

For bladder instillation, the excipient or carrier can be sterile water. The composition can further comprise other active agents, such as steroids or any drugs for treating bladder diseases.

For rectal instillation, the excipient or carrier can be sterile water; thickening agent for adhesion to the rectal surface, such as poloxomer, glycerin, and cellulose derivatives; and suppository base. The composition can further comprise other active agents, such as steroids or any drugs for treating lower bowel diseases.

For nasal instillation, the excipient or carrier can be sterile water, gauze sponge or any device used to insert into the nostril, or an ointment or cream. The composition can further comprise any drugs for treating diseases of the nose.

In certain embodiments, the composition is a transdermal composition. In some specific embodiments, the transdermal composition is a non-oral topical composition. In other specific embodiments, the transdermal composition is a non-mucosal composition. In certain particular embodiments, the transdermal composition is selected from the group consisting of an ointment, a gel, a liniment, a paste, a film, a hydrogel, a liposome, a cream, a patch, and a spray.

In certain embodiment of the methods, an anticoagulant has been or is to be administered to the subject. Non-limiting examples of the anticoagulant include heparin and warfarin.

In certain embodiments, the therapeutically effective amount of the antifibrinolytic is between 1-70% by weight of the composition. In certain particular embodiments, the therapeutically effective amount is between 0.1-10% (e.g., 0.1, 0.2, 0.3, 0.4, 0.5, 0.6, 0.7, 0.8, 0.9, 1, 2, 3, 4, 5, 6, 7, 8, 9, or 10%) by weight of the composition. In one particular embodiment, the therapeutically effective amount is about 2% by weight of the composition.

In other embodiments, the therapeutically effective amount of tranexamic acid is between 1-70% by weight of the composition. In certain particular embodiments, the therapeutically effective amount is between 0.1-10% (e.g., 0.1, 0.2, 0.3, 0.4, 0.5, 0.6, 0.7, 0.8, 0.9, 1, 2, 3, 4, 5, 6, 7, 8, 9, or 10%) by weight of the composition. In one particular embodiment, the therapeutically effective amount is about 2% by weight of the composition.

In other embodiments of the methods, the pharmaceutical composition is administered at the time of injury or while blood is flowing through a wound or cut in the skin or mucosa of a subject. In certain embodiments, the pharmaceutical composition is administered within 5 minutes from the time of injury. In other embodiments, the pharmaceutical composition is administered 0-720 minutes from the time of injury. In other embodiments, the pharmaceutical composition is administered between 0 and 5, 0 and 10, 0 and 15, 0 and 20, 0 and 30, 0 and 40, 0 and 50, 0 and 60, 0 and 120, 0 and 180, 0 and 240, 0 and 300, 0 and 360, 0 and 420, 0 and 480, 0 and 540, 0 and 600, 0 and 660 and 0 and 720 minutes after the time of injury. In other embodiments, the pharmaceutical composition is administered at about 0, 1, 2, 3, 4, 5, 6, 7, 8, 9, 10, 15, 20, 25, 30, 35, 40, 45, 50, 55, 60, 120, 180, 240, 300, 360, 420, 480, 540, 600, 660 or 720 minutes after injury. In other embodiments, the pharmaceutical composition is administered 1-14 days from the time of injury. In other embodiments, the pharmaceutical composition is administered at about 1, 2, 3, 4, 5, 6, 7, 8, 9, 10, 11, 12, 13 or 14 days after the time of injury.

In the methods described herein, the antifibrinolytic is administered at an effective dose. In some embodiments, the effective dose of antifibrinolytic is between 1 and 3000 mg per administration. In other embodiments, the effective dose of antifibrinolytic is between 100 and 1000, 150 and 1000, 200 and 1000, 300 and 1000, 400 and 1000, 500 and 1000, 600 and 1000, 700 and 1000, 800 and 1000, 900 and 1000, 100 and 900, 100 and 800, 100 and 700, 100 and 600, 100 and 500, 100 and 400, 100 and 300, 100 and 200, 200 and 800, 300 and 700, and 400 and 600 mg per administration. In other embodiments, the effective dose of antifibrinolytic is about 100, 200, 300, 400, 500, 600, 700, 800, 900 or 1000 mg per administration.

In the methods described herein, the antifibrinolytic is tranexamic acid. The tranexamic acid can be administered at an effective dose. In some embodiments, the effective dose of tranexamic acid is between 1 and 3000 mg per administration. In other embodiments, the effective dose of tranexamic acid is between 100 and 1000, 150 and 1000, 200 and 1000, 300 and 1000, 400 and 1000, 500 and 1000, 600 and 1000, 700 and 1000, 800 and 1000, 900 and 1000, 100 and 900, 100 and 800, 100 and 700, 100 and 600, 100 and 500, 100 and 400, 100 and 300, 100 and 200, 200 and 800, 300 and 700, and 400 and 600 mg per administration. In other embodiments, the effective dose of tranexamic acid is about 100, 200, 300, 400, 500, 600, 700, 800, 900 or 1000 mg per administration.

In the methods described herein, the antibiotic is administered at an effective dose. In some embodiments, the effective dose of antibiotic is between 1 and 100 mg per administration depending on the antibiotic. In other embodiments, the effective dose of antifibrinolytic is between 1 and 100, 15 and 100, 20 and 100, 30 and 100, 40 and 100, 50 and 100, 60 and 100, 70 and 100, 80 and 100, 90 and 100, 10 and 90, 10 and 80, 10 and 70, 10 and 60, 10 and 50, 10 and 40, 10 and 30, 10 and 20, 20 and 80, 30 and 70, and 40 and 60 mg per administration. In other embodiments, the effective dose of antibiotic is about 10, 20, 30, 40, 50, 60, 70, 80, 90 or 100 mg per administration. In other embodiments, the effective dose of antibiotic is between 100 and 10,000 units per administration depending on the antibiotic. In other embodiments, the effective dose of antifibrinolytic is between 200 and 10,000, 500 and 10,000, 1000 and 10,000, 1500 and 10,000, 2000 and 10,000, 3000 and 10,000, 4000 and 10,000, 5000 and 10,000, 6000 and 10,000, 7000 and 10,000, 8000 and 10,000, 9000 and 10,000, 200 and 9000, 200 and 7000, 200 and 6000, 200 and 5000, 200 and 4000, 200 and 3000, 200 and 3000, 200 and 2000, 200 and 1500, 200 and 1000, 1000 and 9000, 2000 and 8000, and 3000 and 5000 units per administration. In other embodiments, the effective dose of antibiotic is about 100, 1000, 2000, 3000, 4000, 5000, 6000, 7000, 8000, 9000 or 10,000 units per administration.

In certain embodiments, the pharmaceutical composition is left in contact with the cut or wound for between 1 and 120 minutes. In certain embodiments, the pharmaceutical composition is left in contact with the cut or wound for between 1 and 5, 1 and 10, 1 and 15, 1 and 20, 1 and 30, 1 and 40, 1 and 50, 1 and 60, 1 and 120 minutes. In other embodiments, the pharmaceutical composition is left in contact with the cut or wound for about 0, 1, 2, 3, 4, 5, 6, 7, 8, 9, 10, 15, 20, 25, 30, 35, 40, 45, 50, 55, 60, 120 minutes. In other embodiments, the pharmaceutical composition is left in contact with the cut or wound for between 1 and 14 days. In other embodiments, the pharmaceutical composition is left in contact with the cut or wound for about 1, 2, 3, 4, 5, 6, 7, 8, 9, 10, 11, 12, 13 or 14 days.

In certain embodiments, the composition further comprises an amino acid. Non-limiting examples of the amino acid include lysine, histidine, arginine, glycine, methionine, proline, glutamic acid, and arginine.

The pharmaceutical composition can further comprise a preservative. Non-limiting examples of the preservative are benzalkonium chloride, benzethonium chloride, benzoic acid and salts, benzyl alcohol, boric acid and salts, cetylpyridinium chloride, cetyltrimethyl ammonium bromide, chlorobutanol, chlorocresol, chorhexidine gluconate or chlorhexidine acetate, cresol, ethanol, imidazolidinyl urea, metacresol, methylparaben, nitromersol, o-phenyl phenol, parabens, phenol, phenylmercuric acetate/nitrate, propylparaben, sodium benzoate, sorbic acids and salts, β-Phenylethyl alcohol, thimerosal. In particular embodiments, the preservative is benzyl alcohol.

The pharmaceutical composition can be adjusted to a pH of between 4 and 9. In particular embodiments, the pH is adjusted to 6 to 8.

The pharmaceutical composition can be adjusted to be isotonic to 0.3-1.5% sodium chloride. In particular embodiments, the pharmaceutical composition is isotonic to 0.9% sodium chloride.

Pharmaceutical Composition

In another aspect, provided herein is a transdermal pharmaceutical composition comprising an antifibrinolytic. Antifibrinolytics include aminocaproic acid and tranexamic acid. In one embodiment, the antifibrinolytic is co-administered with one or more antibiotics. In another embodiment, the composition further comprises an excipient or carrier that facilitates transdermal administration.

In still another aspect, provided here is a pharmaceutical composition consisting essentially of or consisting of a therapeutically effective amount of tranexamic acid, one or more antibiotics, and an excipient or carrier that facilitates local administration.

In one particular embodiment, provided herein is a transdermal pharmaceutical composition consisting essentially of or consisting of a therapeutically effective amount of tranexamic acid, one or more antibiotics, and an excipient or carrier that facilitates transdermal administration.

In certain embodiments of the compositions described above, the one or more antibiotics are antibiotics that are effective when administered locally. Non-limiting examples of the antibiotics described herein include sulfacetamide, mupirocin, erythromycin, sulfadiazine, mafenide, tetracycline, bacitracin, neomycin, and polymyxin B.

In other embodiments, the one or more antibiotics are a triple antibiotic. The triple antibiotic can include bacitracin, neomycin, and polymyxin B.

According to certain embodiments, the compositions described herein are administered topically. In other embodiments, they are administered transdermally. In other embodiments, the compositions described herein are administered at the site of a wound or cut of the skin or mucosa from which blood is flowing.

In certain embodiments, the excipient or carrier permits the composition to remain in contact with a bleeding wound. In certain particular embodiments, the excipient or carrier comprises an ointment, a cream, a liniment, a paste, a patch, a lotion, a gel, a shampoo, a hydrogel, a liposome, a spray, an aerosol, a solution, a sponge, a film, a plaster, a surgical dressing, a bandage, or an emulsion.

If the compositions of the disclosure are to be administered topically, the compositions can be formulated in the form of an ointment, cream, patch such as transdermal patch, lotion, gel, shampoo, spray, aerosol, solution, sponge, film, plaster, surgical dressing, bandage, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as FREON®) or in a squeeze bottle. Moisturizers or humectants can also be added to pharmaceutical compositions and dosage forms if desired. Examples of such additional ingredients are well known in the art.

In certain embodiments, the antifibrinolytic is between 1 and 70% by weight of the pharmaceutical composition. In particular embodiments, the therapeutically effective amount is between 0.1-10% (e.g., 0.1, 0.2, 0.3, 0.4, 0.5, 0.6, 0.7, 0.8, 0.9, 1, 2, 3, 4, 5, 6, 7, 8, 9, or 10%) by weight of the composition. In one particular embodiment, the therapeutically effective amount is about 2% by weight of the composition.

In other embodiments, the tranexamic acid is between 1 and 70% by weight of the pharmaceutical composition. In particular embodiments, the therapeutically effective amount is between 0.1-10% (e.g., 0.1, 0.2, 0.3, 0.4, 0.5, 0.6, 0.7, 0.8, 0.9, 1, 2, 3, 4, 5, 6, 7, 8, 9, or 10%) by weight of the composition. In one particular embodiment, the therapeutically effective amount is about 2% by weight of the composition.

In certain particular embodiments, the excipient or carrier comprises cocoa butter, cottonseed oil, sodium pyruvate, tocopheryl acetate, and petroleum jelly.

In certain particular embodiments, the composition comprises an excipient or carrier that permits instillation of the composition, such as nasal instillation, rectal instillation, and bladder instillation.

For bladder instillation, the excipient or carrier can be sterile water. The composition can further comprise other active agents, such as steroids or any drugs for treating bladder diseases.

For rectal instillation, the excipient or carrier can be sterile water; thickening agent for adhesion to the rectal surface, such as poloxamer, glycerin, and cellulose derivatives; and suppository base. The composition can further comprise other active agents, such as steroids or any drugs for treating lower bowel diseases.

For nasal instillation, the excipient or carrier can be sterile water, gauze sponge or any device used to insert into the nostril, or an ointment or cream. The composition can further comprise any drugs for treating diseases of the nose.

In certain embodiments, the composition is a transdermal composition. In some specific embodiments, the transdermal composition is a non-oral topical composition. In other specific embodiments, the transdermal composition is a non-mucosal composition. In certain particular embodiments, the transdermal composition is selected from the group consisting of an ointment, a gel, a liniment, a paste, a film, a hydrogel, a liposome, a cream, a patch, and a spray.

In certain embodiments, the composition is administered to a subject in need thereof to which an anticoagulant has been or is to be administered. Non-limiting examples of the anticoagulant include heparin and warfarin.

In certain embodiments, the composition further comprises an amino acid. Non-limiting examples of the amino acid include lysine, histidine, arginine, glycine, methionine, proline, glutamic acid, and arginine.

The pharmaceutical composition can further comprise a preservative. Non-limiting examples of the preservative are benzalkonium chloride, benzethonium chloride, benzoic acid and salts, benzyl alcohol, boric Acid and salts, cetylpyridinium chloride, cetyltrimethyl ammonium bromide, chlorobutanol, chlorocresol, chorhexidine gluconate or chlorhexidine acetate, cresol, ethanol, imidazolidinyl urea, metacresol, methylparaben, nitromersol, o-phenyl phenol, parabens, phenol, phenylmercuric acetate/nitrate, propylparaben, sodium benzoate, sorbic acids and salts, β-Phenylethyl alcohol, thimerosal. In particular embodiments, the preservative is benzyl alcohol.

The pharmaceutical composition can be adjusted to a pH of between 4 and 9. In particular embodiments, the pH is adjusted to 6 to 8.

The pharmaceutical composition can be adjusted to be isotonic to 0.3-1.5% sodium chloride. In particular embodiments, the pharmaceutical composition is isotonic to 0.9% sodium chloride.

Kit

In still another aspect, provided herein is a kit comprising:

a pharmaceutical composition comprising a therapeutically effective amount of an antifibrinolytic;

an excipient or carrier that facilitates transdermal administration;

two or more containers for housing the composition and excipient or carrier; and instructions for use.

Antifibrinolytics include aminocaproic acid and tranexamic acid. In one embodiment, the antifibrinolytic is co-administered with one or more antibiotics.

In yet another aspect, provided herein is a kit comprising:

a pharmaceutical composition consisting essentially of or consisting of a therapeutically effective amount of tranexamic acid, and one or more antibiotics;

an excipient or carrier that facilitates local administration;

two or more containers for housing the composition and excipient or carrier; and instructions for use.

In one particular embodiment, provided herein is a kit comprising a pharmaceutical composition consisting essentially of or consisting of a therapeutically effective amount of tranexamic acid and one or more antibiotics; an excipient or carrier that facilitates transdermal administration; two or more containers for housing the composition and the excipient or carrier; and instructions for use.

In certain embodiments, the therapeutically effective amount of the antifibrinolytic is between 1-70% by weight of the composition. In certain particular embodiments, the therapeutically effective amount is between 0.1-10% (e.g., 0.1, 0.2, 0.3, 0.4, 0.5, 0.6, 0.7, 0.8, 0.9, 1, 2, 3, 4, 5, 6, 7, 8, 9, or 10%) by weight of the composition. In one particular embodiment, the therapeutically effective amount is about 2% by weight of the composition.

In other embodiments, the therapeutically effective amount of tranexamic acid is between 1-70% by weight of the composition. In certain particular embodiments, the therapeutically effective amount is between 0.1-10% (e.g., 0.1, 0.2, 0.3, 0.4, 0.5, 0.6, 0.7, 0.8, 0.9, 1, 2, 3, 4, 5, 6, 7, 8, 9, or 10%) by weight of the composition. In one particular embodiment, the therapeutically effective amount is about 2% by weight of the composition.

In certain embodiments, the one or more antibiotics are the antibiotics that are effective when administered locally. The antibiotics can be sulfacetamide, mupirocin, erythromycin, sulfadiazine, mafenide, tetracycline, bacitracin, neomycin, and polymyxin B.

In other embodiments, the one or more antibiotics are a triple antibiotic. The triple antibiotic can be bacitracin, neomycin, and/or polymyxin B.

In still other embodiments, the excipient or carrier permits the composition to remain in contact with a bleeding wound. In certain particular embodiments, the excipient or carrier comprises an ointment, a cream, a liniment, a paste, a patch, a lotion, a gel, a shampoo, a hydrogel, a liposome, a spray, an aerosol, a solution, a sponge, a film, a plaster, a surgical dressing, a bandage, or an emulsion.

According to certain embodiments, the compositions described herein are administered topically. In other embodiments, they are administered transdermally. In other embodiments, the compositions described herein are administered at the site of a wound or cut of the skin or mucosa from which blood is flowing.

In certain particular embodiments, the excipient or carrier comprises cocoa butter, cottonseed oil, sodium pyruvate, tocopheryl acetate, and petroleum jelly.

In certain particular embodiments, the kit comprises an excipient or carrier that permits instillation of the composition, such as nasal instillation, rectal instillation, and bladder instillation.

For bladder instillation, the excipient or carrier can be sterile water. The composition can further comprise other active agents, such as steroids or any drugs for treating bladder diseases.

For rectal instillation, the excipient or carrier can be sterile water; thickening agent for adhesion to the rectal surface, such as poloxamer, glycerin, and cellulose derivatives; and suppository base. The composition can further comprise other active agents, such as steroids or any drugs for treating lower bowel diseases.

For nasal instillation, the excipient or carrier can be sterile water, gauze sponge or any device used to insert into the nostril, or an ointment or cream. The composition can further comprise any drugs for treating diseases of the nose.

In certain embodiments, the composition is a transdermal composition. In some specific embodiments, the transdermal composition is a non-oral topical composition. In other specific embodiments, the transdermal composition is a non-mucosal composition. In certain particular embodiments, the transdermal composition is selected from the group consisting of an ointment, a gel, a liniment, a paste, a film, a hydrogel, liposomes, a cream, a patch, and a spray.

In certain embodiments, the composition is administered to a subject in need thereof to which an anticoagulant has been or is to be administered. Non-limiting examples of the anticoagulant include heparin and warfarin.

In certain embodiments, the excipient or carrier is an apparatus for topical administration, wherein the apparatus is selected from the group consisting of a patch, a sponge, a film, a surgical dressing, a spray, and a bandage.

In certain embodiments, the composition further comprises an amino acid. Non-limiting examples of the amino acid include lysine, histidine, arginine, glycine, methionine, proline, glutamic acid, and arginine.

The pharmaceutical composition of the kits described above can further comprise a preservative. Non-limiting examples of the preservative are benzalkonium chloride, benzethonium chloride, benzoic acid and salts, benzyl alcohol, boric Acid and salts, cetylpyridinium chloride, cetyltrimethyl ammonium bromide, chlorobutanol, chlorocresol, chorhexidine gluconate or chlorhexidine acetate, cresol, ethanol, imidazolidinyl urea, metacresol, methylparaben, nitromersol, o-phenyl phenol, parabens, phenol, phenylmercuric acetate/nitrate, propylparaben, sodium benzoate, sorbic acids and salts, β-Phenylethyl alcohol, thimerosal. In particular embodiments, the preservative is benzyl alcohol.

The pharmaceutical composition of the kits described above can be adjusted to a pH of between 4 and 9. In particular embodiments, the pH is adjusted to 6 to 8.

The pharmaceutical composition of the kits described above can be adjusted to be isotonic to 0.3-1.5% sodium chloride. In particular embodiments, the pharmaceutical composition is isotonic to 0.9% sodium chloride.

EXAMPLES

I. Topical Compositions

| | |
|---|---|
| Composition 1 | 1. Antibiotic (active)<br>2. Tranexamic acid 2% (active)<br>3. Ointment base qs ad |
| Composition 2 | 1. Tranexamic acid 0.1%-10%<br>2. Ointment base qs ad |
| Composition 3 | 1. Tranexamic acid 0.1-10%<br>2. Preservative qs ad<br>3. Isotonic adjuster to 0.9% sodium chloride<br>4. pH adjuster or buffer qs<br>5. Sterile water for injection qs ad |
| Composition 4 | 1. Tranexamic acid 0.1-10%<br>2. Preservative qs ad<br>3. Isotonic adjuster to 0.9% sodium chloride<br>4. pH adjuster or buffer qs<br>5. Sterile water for injection qs ad<br>6. Gauze sponge or any device used to apply to the skin or mucus membranes |
| Composition 5 | 1. Tranexamic acid 0.1-10%<br>2. Additional active agent, such as an antibiotic or any other drug for the treatment of diseases of the skin or mucus membranes<br>3. Preservative qs ad<br>4. Isotonic adjuster to 0.9% sodium chloride<br>5. pH adjuster or buffer qs<br>6. Sterile water for injection qs ad |
| Composition 6 | 1. Tranexamic acid 0.1-10%<br>2. Additional active agent, such as an antibiotic or any other drug for the treatment of diseases of the skin or mucus membranes<br>3. Preservative qs ad<br>4. Isotonic adjuster to 0.9% sodium chloride<br>5. pH adjuster or buffer qs<br>6. Sterile water for injection qs ad<br>7. Gauze sponge or any device used to apply to the skin or mucus membranes |

II. Bladder Instillation Compositions

| | |
|---|---|
| Composition 3 | 1. Tranexamic acid 0.1-10%<br>2. Preservative qs ad<br>3. Isotonic adjuster to 0.9% sodium chloride<br>4. pH adjuster or buffer qs<br>5. Sterile water for injection qs ad |
| Composition 7 | 1. Tranexamic acid 0.1-10%<br>2. Additional active agent, such as an antibiotic, steroid or any other drug for the treatment of diseases of the bladder.<br>3. Preservative qs ad<br>4. Isotonic adjuster to 0.9% sodium chloride<br>5. pH adjuster or buffer qs<br>6. Sterile water for injection qs ad |

III. Rectal Instillation Compositions

| | |
|---|---|
| Composition 3 | 1. Tranexamic acid 0.1-10%<br>2. Preservative qs ad<br>3. Isotonic adjuster to 0.9% sodium chloride<br>4. pH adjuster or buffer qs<br>5. Sterile water for injection qs ad |
| Composition 8 | 1. Tranexamic acid 0.1-10%<br>2. Preservative qs ad<br>3. Isotonic adjuster to 0.9% sodium chloride<br>4. pH adjuster or buffer qs<br>5. Sterile water for injection qs ad<br>6. Thickening agent for adhesion to the rectal surface, such as poloxomer, glycerin, cellulose derivatives, etc. qs ad |
| Composition 9 | 1. Tranexamic acid 0.1-10%<br>2. Preservative qs ad<br>3. Isotonic adjuster to 0.9% sodium chloride<br>4. pH adjuster or buffer qs<br>5. suppository base qs ad |
| Composition 10 | 1. Tranexamic acid 0.1-10%<br>2. Additional active agent, such as an antibiotic, steroid or any other drug for the treatment of diseases of the lower bowel<br>3. Preservative qs ad<br>4. Isotonic adjuster to 0.9% sodium chloride<br>5. pH adjuster or buffer qs<br>6. Sterile water for injection qs ad |
| Composition 11 | 1. Tranexamic acid 0.1-10%<br>2. Additional active agent, such as an antibiotic, steroid or any other drug for the treatment of diseases of the lower bowel<br>3. Preservative qs ad<br>4. Isotonic adjuster to 0.9% sodium chloride<br>5. pH adjuster or buffer qs<br>6. suppository base qs ad |

IV. Nasal Instillation Compositions

| | |
|---|---|
| Composition 3 | 1. Tranexamic acid 0.1-10%<br>2. Preservative qs ad<br>3. Isotonic adjuster to 0.9% sodium chloride<br>4. pH adjuster or buffer qs<br>5. Sterile water for injection qs ad |
| Composition 12 | 1. Tranexamic acid 0.1-10%<br>2. Preservative qs ad<br>3. Isotonic adjuster to 0.9% sodium chloride<br>4. pH adjuster or buffer qs<br>5. Sterile water for injection qs ad<br>6. Gauze sponge or any device used to insert into the nostril |
| Composition 13 | 1. Tranexamic acid 0.1-10%<br>2. Additional active agent, such as an antibiotic or any other drug for the treatment of diseases of the nose<br>3. Preservative qs ad<br>4. Isotonic adjuster to 0.9% sodium chloride<br>5. pH adjuster or buffer qs<br>6. Sterile water for injection qs ad |
| Composition 14 | 1. Tranexamic acid 0.1-10%<br>2. Additional active agent, such as an antibiotic or any other drug for the treatment of diseases of the nose.<br>3. Preservative qs ad<br>4. Isotonic adjuster to 0.9% sodium chloride<br>5. pH adjuster or buffer qs<br>6. Sterile water for injection qs ad<br>7. Gauze sponge or any device used to insert into the nostril |
| Composition 15 | 1. Tranexamic acid 0.1-10%<br>2. Additional active agent, such as an antibiotic or any other drug for the treatment of diseases of the nose.<br>3. Preservative qs ad<br>4. Isotonic adjuster to 0.9% sodium chloride<br>5. pH adjuster or buffer qs<br>6. ointment or cream base qs ad |
| Composition 16 | 1. Tranexamic acid 0.1-10%<br>2. Additional active agent, such as an antibiotic or any other drug for the treatment of diseases of the nose.<br>3. Preservative qs ad<br>4. Isotonic adjuster to 0.9% sodium chloride<br>5. pH adjuster or buffer qs<br>6. ointment or cream base qs ad<br>7. Gauze sponge or any device used to insert into the nostril |

V. Preparation of a Composition of Triple Antibiotic with Tranexamic Acid 2% w/w Ointment An exemplary process to make the composition includes the following steps:

1. weight half of the triple antibiotic ointment into an EMP;
2. place the tranexamic acid into the EMP on top of the triple antibiotic ointment;
3. place the rest of the triple antibiotic ointment into the EMP;
4. drill 2:00/5, do not mill;
5. package 15 gram into 1 oz ointment tubes and cut the excess tube off; and
6. label (expires in 6 months; may be used as Rx or OTC).

VI. Preparation of a Composition of Antibiotic with Tranexamic Acid 5% w/w Ointment Another exemplary process to make the composition included the following steps:

1. one half (about 47.5 g) of the bacitracin zinc ointment was weighed into an EMP;
2. about 5 g of the tranexamic acid was added into the EMP on top of the bacitracin zinc ointment;
3. the rest of the bacitracin zinc ointment (about 47.5 g) was added into the EMP;
4. 2:00/5 was drilled, with no milling;
5. about 15 g of the product was package into 1 oz ointment tubes and the excess tube was cut off;
6. label was attached indicated the expiration time as 6 months and the product may be used as Rx or OTC.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

INCORPORATION BY REFERENCE

The entire contents of all patents, published patent applications and other references cited herein are hereby expressly incorporated herein in their entireties by reference.

The invention claimed is:

1. A pharmaceutical composition consisting essentially of a therapeutically effective amount of:
   (a) tranexamic acid;
   (b) one or more antibiotic(s);
   (c) optionally, one or more anesthetic(s);
   (d) optionally, one or more non-steroid anti-inflammatory drug(s) selected from the group consisting of ketorolac, ketoprofen, flurbiprofen, bromfenac, diclofenac and combinations thereof; and
   (e) an excipient or carrier that facilitates transdermal non-mucosal administration.

2. The pharmaceutical composition of claim 1, wherein the therapeutically effective amount of tranexamic acid is between 1-70% by weight of the composition.

3. The pharmaceutical composition of claim 1, wherein the one or more antibiotic(s) are selected from the group consisting of sulfacetamide, mupirocin, erythromycin, sulfadiazine, mafenide, tetracycline, bacitracin, neomycin, and polymyxin B.

4. The pharmaceutical composition of claim 1, wherein the one or more antibiotic(s) are selected from the group consisting of bacitracin, neomycin, and polymyxin B.

5. The pharmaceutical composition of claim 1, wherein the excipient or carrier permits the composition to remain in contact with a bleeding wound.

6. The pharmaceutical composition of claim 5, wherein the excipient or carrier comprises an ointment, a cream, a liniment, a paste, a patch, a lotion, a gel, a shampoo, a hydrogel, a liposome, a spray, an aerosol, a solution, a sponge, a film, a plaster, a surgical dressing, a bandage, or an emulsion.

7. The pharmaceutical composition of claim 1, wherein the one or more anesthetic(s) are selected from the group consisting of lidocaine, proparacaine, procaine, tetracaine and combinations thereof.

8. The pharmaceutical composition of claim 1, wherein the transdermal non-mucosal composition is selected from the group consisting of an ointment, a gel, a liniment, a paste, a film, a hydrogel, a liposome, a cream, a patch, and a spray.

9. A method for treating bleeding in a subject in need thereof comprising transdermally non-mucosally administering to the subject a pharmaceutical composition of claim 1.

10. The method of claim 9, wherein the therapeutically effective amount of tranexamic acid is between 1-70% by weight of the composition.

11. The method of claim 9, wherein the one or more antibiotics are selected from the group consisting of sulfacetamide, mupirocin, erythromycin, sulfadiazine, mafenide, tetracycline, bacitracin, neomycin, and polymyxin B.

12. The method of claim 9, wherein the one or more antibiotics are bacitracin, neomycin, and/or polymyxin B.

13. The method of claim 9, wherein an anticoagulant has been or is to be administered to the subject.

14. The method of claim 9, wherein the excipient or carrier permits the composition to remain in contact with said bleeding wound.

15. The method of claim 14, wherein the excipient or carrier comprises an ointment, a cream, a liniment, a paste, a patch, a lotion, a gel, a shampoo, a hydrogel, a liposome, a spray, an aerosol, a solution, a sponge, a film, a plaster, a surgical dressing, a bandage, or an emulsion.

16. The method of claim 9, wherein the one or more anesthetic(s) are selected from the group consisting of lidocaine, proparacaine, procaine, tetracaine and combinations thereof.

17. The method of claim 9, wherein the one or more non-steroid anti-inflammatory drug(s) are selected from the group consisting of ketorolac, ketoprofen, flurbiprofen, bromfenac, diclofenac and combinations thereof.

18. The method of claim 9, wherein the transdermal non-mucosal composition is selected from the group consisting of an ointment, a gel, a liniment, a paste, a film, a hydrogel, a liposome, a cream, a patch and a spray.

19. A kit comprising:
   the pharmaceutical composition of claim 1;
   two or more containers for housing the composition; and
   instructions for use.

20. A pharmaceutical composition consisting of a therapeutically effective amount of tranexamic acid and an excipient or carrier that facilitates transdermal non-mucosal administration.

21. The pharmaceutical composition of claim 20, further comprising one or more antibiotics.

22. The pharmaceutical composition of claim 20, wherein the therapeutically effective amount of tranexamic acid is between 1-70% by weight of the composition.

23. The pharmaceutical composition of claim 21, wherein the one or more antibiotics are selected from the group consisting of sulfacetamide, mupirocin, erythromycin, sulfadiazine, mafenide, tetracycline, bacitracin, neomycin, and polymyxin B.

24. The pharmaceutical composition of claim 21, wherein the one or more antibiotics are selected from the group consisting of bacitracin, neomycin, and polymyxin B.

25. The pharmaceutical composition of claim 20, wherein the excipient or carrier permits the composition to remain in contact with a bleeding wound.

26. The pharmaceutical composition of claim 25, wherein the excipient or carrier comprises an ointment, a cream, a liniment, a paste, a patch, a lotion, a gel, a shampoo, a hydrogel, a liposome, a spray, an aerosol, a solution, a sponge, a film, a plaster, a surgical dressing, a bandage, or an emulsion.

27. The pharmaceutical composition of claim 20, wherein the composition is an ointment, a gel, a liniment, a paste, a film, a hydrogel, a liposome, a cream, a patch, or a spray.

28. A method for treating bleeding in a subject in need thereof comprising transdermally non-mucosally administering to the subject a pharmaceutical composition, wherein the composition consists of a therapeutically effective amount of tranexamic acid and an excipient or carrier that facilitates the transdermal non-mucosal administration.

29. The method of claim 28, wherein the pharmaceutical composition further comprises one or more antibiotics.

30. The method of claim 28, wherein the pharmaceutical composition consists essentially of a therapeutically effective amount of tranexamic acid, one or more antibiotics, and an excipient or carrier that facilitates transdermal non-mucosal administration.

31. The method of claim 28, wherein the therapeutically effective amount of tranexamic acid is between 1-70% by weight of the composition.

32. The method of claim 29, wherein the one or more antibiotics are selected from the group consisting of sulfacetamide, mupirocin, erythromycin, sulfadiazine, mafenide, tetracycline, bacitracin, neomycin, and polymyxin B.

33. The method of claim 29, wherein the one or more antibiotics are bacitracin, neomycin, and/or polymyxin B.

34. The method of claim 28, wherein an anticoagulant has been or is to be administered to the subject.

35. The method of claim 28, wherein the excipient or carrier permits the composition to remain in contact with said bleeding wound.

36. The method of claim 35, wherein the excipient or carrier comprises an ointment, a cream, a liniment, a paste, a patch, a lotion, a gel, a shampoo, a hydrogel, a liposome, a spray, an aerosol, a solution, a sponge, a film, a plaster, a surgical dressing, a bandage, or an emulsion.

37. The method of claim 28, wherein the composition is an ointment, a gel, a liniment, a paste, a film, a hydrogel, a liposome, a cream, a patch, or a spray.

38. A kit comprising: a pharmaceutical composition comprising a therapeutically effective amount of tranexamic acid; an excipient or carrier that facilitates transdermal non-mucosal administration; two or more containers for housing the composition and the excipient or carrier; and instructions for use.

39. The pharmaceutical composition of claim 1, consisting essentially of a therapeutically effective amount of:
  (a) tranexamic acid;
  (b) one or more antibiotic(s);
  (c) one or more anesthetic(s);
  (d) one or more non-steroid anti-inflammatory drug(s) selected from the group consisting of ketorolac, ketoprofen, flurbiprofen, bromfenac, diclofenac and combinations thereof; and
  (e) an excipient or carrier that facilitates transdermal non-mucosal administration.

* * * * *